US011684405B2

(12) United States Patent
Schulz et al.

(10) Patent No.: US 11,684,405 B2
(45) Date of Patent: Jun. 27, 2023

(54) APPARATUS AND METHOD FOR GENERATING A PLASMA IN AN AQUEOUS ENVIRONMENT

(71) Applicant: Erbe Elektromedizin GmbH, Tuebingen (DE)

(72) Inventors: Florian Schulz, Rottenburg a.N. (DE); Michael Sauter, Albstadt (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 781 days.

(21) Appl. No.: 16/410,096

(22) Filed: May 13, 2019

(65) Prior Publication Data

US 2019/0343572 A1 Nov. 14, 2019

(30) Foreign Application Priority Data

May 14, 2018 (EP) ..................................... 18172105

(51) Int. Cl.
*A61B 18/12* (2006.01)
*A61B 18/04* (2006.01)
(Continued)

(52) U.S. Cl.
CPC ........ *A61B 18/042* (2013.01); *A61B 18/1206* (2013.01); *H05H 1/46* (2013.01);
(Continued)

(58) Field of Classification Search
CPC .................. A61B 18/12; A61B 18/042; A61B 2018/00577; A61B 2018/00702;
(Continued)

(56) References Cited

U.S. PATENT DOCUMENTS 10,052,146 B2 8/2018 Canady et al.
10,342,595 B2 7/2019 Hancock et al.
(Continued)

FOREIGN PATENT DOCUMENTS

CN 105592886 A 5/2016
DE 102014217362 A1 3/2016
(Continued)

OTHER PUBLICATIONS

"Electrical Impedance", Jun. 29, 2022, Encyclopaedia Britannica, https://www.britannica.com/science/electrical-impedance (Year: 2022).*
(Continued)

*Primary Examiner* — Michael F Peffley
*Assistant Examiner* — Samantha M Good
(74) *Attorney, Agent, or Firm* — Fitch, Even, Tabin & Flannery LLP

(57) ABSTRACT

An apparatus (14) for supplying a medical instrument (15) for the treatment of biological tissue (11) due to the action of a plasma (28) is disposed, in accordance with the invention, in a special manner for the ignition and the stable development of a plasma (28) on the electrode (27) of the instrument (15). To accomplish this, the apparatus (14) comprises a control device (23) that, during an ignition test, limits—preferably in an instrument-specific manner—the current deliverable to the instrument (15) and/or limits the electrical power to be output to the instrument (15), and/or, in doing so, works with a reduced operating voltage. With this measure, a rapid, stable plasma development with minimal spark play is achieved with a large variety of connectable instruments (15a-15e).

14 Claims, 3 Drawing Sheets

(51) Int. Cl.
*H05H 1/46* (2006.01)
*A61B 18/00* (2006.01)
(52) U.S. Cl.
CPC ............... *A61B 2018/00702* (2013.01); *A61B 2018/00875* (2013.01)
(58) Field of Classification Search
CPC .. A61B 2018/0072; A61B 2018/00767; A61B 2018/00875; A61B 2018/1213; A61B 2018/1472; A61B 18/1206; H05H 1/46
See application file for complete search history.

(56) References Cited

U.S. PATENT DOCUMENTS

| | | |
|---|---|---|
| 2002/0022836 A1 | 2/2002 | Goble et al. |
| 2004/0049180 A1 | 3/2004 | Sharps et al. |
| 2005/0177150 A1 | 8/2005 | Amoah et al. |
| 2012/0271304 A1 | 10/2012 | Werner |
| 2014/0309632 A1 | 10/2014 | Ogata et al. |
| 2016/0302843 A1 | 10/2016 | Ishikawa et al. |
| 2017/0202616 A1 | 7/2017 | Pate et al. |

FOREIGN PATENT DOCUMENTS

| | | |
|---|---|---|
| DE | 102017110473 A1 | 11/2018 |
| EP | 2108325 A1 | 10/2009 |
| EP | 2514380 A1 | 10/2012 |
| JP | 2012-223585 A | 11/2012 |
| JP | 2016-513579 A | 5/2016 |
| RU | 2138213 C1 | 9/1999 |
| RU | 122280 U1 | 11/2012 |
| RU | 2603296 C2 | 11/2016 |
| WO | 2016030511 A1 | 3/2016 |

OTHER PUBLICATIONS

European Search Report dated Nov. 26, 2018, in corresponding European Patent Application No. 18172105.1 (7 pages).
Russian Office Action and Search Report dated Dec. 27, 2021, in corresponding Russian Application No. 2019113720/14(026466), with English translation (9 pages).
Chinese Office Action dated Feb. 28, 2022, in corresponding Chinese Application No. 201910398534.7, with English translation (16 pages).
Japanese Patent Office, Notice of Reasons for Refusal for Japanese Patent Application No. 2019-089481, dated Oct. 27, 2022, 11 pages.
European Patent Office, Office Action dated Feb. 23, 2023 for European Patent No. 18172105-1.1113; 10 pages.

* cited by examiner

APPARATUS AND METHOD FOR GENERATING A PLASMA IN AN AQUEOUS ENVIRONMENT

RELATED APPLICATION(S)

This application claims the benefit of European Patent Application No. 18172105.1, filed May 14, 2018, the contents of which is incorporated herein by reference as if fully rewritten herein.

TECHNICAL FIELD

The invention relates to an apparatus for supplying a medical instrument for the treatment of biological tissue due to the action of a plasma and to a method for igniting and maintaining a plasma in an aqueous environment.

BACKGROUND

Medical instruments that act on biological tissue by means of a plasma emitted by an electrode have basically been known and in use.

Regarding this, e.g., publication EP 2 514 380 A1 discloses an electric scalpel that is disposed for cutting biological tissue. To accomplish this, a spatula-shaped electrode is used to generate a plasma that is referred to as the spark that acts on the tissue in a cutting manner The plasma is ignited in an aqueous moist environment in that initially water on the electrode is evaporated and then the spark is ignited in the vapor layer. In order to generate the required vapor layer and thus achieve drying of the electrode as rapidly as possible, work is performed at a higher pulse-pause ratio of the pulse-width-modulated RF voltage during this warm-up phase, while work is performed at a lower pulse-pause ratio during the subsequent cutting operation.

Publication DE 10 2014 217 362 A1 deals with plasma vaporization by means of an instrument referred to as a resectoscope that is supplied by an RF surgical apparatus. During the surgical procedure to be performed with the latter, the instrument is located, as a rule, in a saline solution that is used as rinsing fluid. By applying the RF voltage to the vaporization electrode of the instrument, a plasma is ignited. To do so, initially a vapor layer is generated around the vaporization electrode, this requiring high output and currents that can strongly heat the rinsing fluid and thus the surrounding biological tissue. In order to avoid a strong heating of the rinsing fluid and, at the same time, facilitate plasma ignition, a barrier device is provided with which the rinsing fluid flow rate in a rinsing fluid line can be blocked or decreased. This is intended not only to facilitate plasma ignition but also to minimize the energy input of the ignition process.

In order to perform tissue resections, different instruments with different electrode forms can be made available to the user, said instruments exhibiting different ignition willingnesses and different plasma maintenance abilities. Furthermore, when the plasma is ignited, occasional neuromuscular stimulations can be recorded, which may irritate the user or interfere with the treatment process. Plasma instabilities or excessive spark play during ignition can likewise have an equally disruptive effect.

It is the object of the invention to state an apparatus and a method that correct at least one of the aforementioned aspects.

SUMMARY

This object is achieved with the device or apparatus as described below, as well as with the method as described below:

The apparatus includes a device that comprises a generator for the delivery of a high-frequency ac voltage, as well as a power supply that is connected to the generator in order to provide said generator with the operating voltage. The generator is connected to an outlet that can be connected to an instrument. Furthermore, the apparatus comprises a measuring device for determining the electrical resistance of the instrument that is connected to the outlet. In doing so, the resistance of the instrument is understood to mean any parameter that may be understood as the quotient of the voltage applied to the outlet and the current flowing through the instrument when dc voltage is being used for measurement. When ac voltage is used for measurement, the resistance is the real component of the impedance that is the quotient of voltage and current. Instead of the resistance in the present invention, it is also possible to always use the impedance, the apparent resistance, the reactance or the active resistance. The resistance of the instrument is thus essentially defined by the transition resistance from the electrode to the aqueous environment as well as the resistance of the aqueous environment itself up to the return electrode.

Furthermore, the apparatus comprises a control device that is disposed to specify the operating voltage and/or the power that can be delivered to the instrument, and/or the maximum current consistent with the measured resistance for at least a period of time, that can be delivered to the instrument and, in doing so, appropriately control the power supply and/or the generator. The said period of time may in particular be a specified period of time that is variable or constant, said period of time being provided as the ignition test time for the development of a plasma.

Furthermore, the control device may be disposed to provide—upon expiration of the ignition test time—different specifications for the operating voltage and/or the power that can be delivered to the instrument and/or the maximum current that can be delivered to the instrument, said specifications deviating from the specifications of the ignition test time.

With the specific specification of the voltage (i.e., the parameter) of the high-frequency dc voltage and/or the operating voltage for the ignition test time provided by the power supply and/or with the limitation of the power during the ignition test time, and/or the limitation of the current that can be delivered by the power supply and/or the high-frequency generator—each in view of the measured minimum resistance of the electrode that is immersed in the fluid but not ignited—an adaptation of the ignition process to the different instruments can be achieved with different electrode forms. In doing so it has been found that a reproducible interrelationship exists between the minimal resistance to be measured on the instrument and those values for the operating voltage, the maximum power and/or the maximum current, with which a safe and stable plasma ignition with minimal spark play and minimum—or at least minor—neuromuscular stimulations can be achieved.

In particular, it has been found that, due to the specific setting of the operating voltage for the ignition time, in particular the determination of an operating voltage that is higher (e.g., nominal value of max. 550 Vp (Vp stands for peak voltage) than the operating voltage (e.g., max. 460 Vp) required later for maintaining the plasma, neuromuscular stimulations can be minimized, and a lower ignition spark intensity is obvious during the transition from the non-ignited state to the formation of the plasma. Likewise, the limitation of the maximum current flowing with the wet electrode without sparks, as well as the power for the ignition operation, in particular the instrument-specific limitation of the maximum current and the maximum power, act in an attenuating manner up to an eliminating manner in view of neuromuscular stimulations.

Within the stated meaning, a current limitation and/or a power limitation, i.e., the limitation of the maximum current at the power supply or at the high-frequency generator, can contribute to the improvement of the ignition process and plasma stabilization, in that the formation of excessively large vapor bubbles and the release of same from the electrode of the instrument are avoided.

For control of the operating voltage the power supply may comprise a voltage regulation input that is connected to the control device. Via this voltage regulation input, the operating voltage to be delivered by the power supply is specified. However, it must be expected that—despite the control loop typically existing in the power supply for adjusting the desired operating voltage—there may occur operating voltage fluctuations on the outlet of the power supply, i.e., in particular voltage changes due to rapid load changes. Load changes cause an increase of the operating voltage output by the power supply due to the energy stored in the output filter of the power supply. Furthermore, the voltage changes can be due to the finite reaction time of the voltage regulation loop provided in the power supply. With a limitation of the operating voltage during the ignition operation to a reduced value, it can be achieved that—due to the ignition of the plasma—a surge-like resistance increase on the electrode and thus surge-like current reduction leads to an excessive short-time increase of he operating voltage. As a result of this, it is possible during the transition phase (meaning during the transition from the quasi short circuit with the wet electrode to vapor and plasma formation) an excess increase of the power input can be avoided. At the same time bubble formation is reduced and the plasma thus stabilized. Consequently, excessive spark play like undesirable neuromuscular stimulation can be avoided or reduced.

Alternatively or additionally, the power supply and/or the generator comprise a current-limiting inlet that is connected to the control device. In doing so, the maximum current that can be delivered by the instrument and thus the current with non-ignited—plasma, said current flowing from the instrument into the surrounding aqueous fluid, are limited. On the one hand, this limits the power input into the fluid and the tissue and also stabilizes the plasma ignition process.

Additionally or alternatively, the power supply and/or the generator may comprise a power limitation inlet that is connected to the control device. The signal output to the power limitation inlet specifies the maximum power that can be delivered by the generator. The power limitation that can be effected in this manner avoids tissue damage, instrument damage and an excessive spark play and stabilizes the ignition process.

The control device may comprise an operating status detection device that is disposed to detect the start of an ignition test. If such a test is detected, the control device can specify a nominal value for the operating voltage during the ignition test, said value being greater than the nominal value during the operation with a stable plasma following the ignition test.

The operating status detection device may also be disposed to differentiate at the end of an ignition test whether a stable plasma was ignited or whether no plasma is present. Based on this information, it is possible to control further operation of the apparatus. If a stable plasma development was detected, additional ignition tests are prevented, and the operating voltage and/or the maximum power and/or the maximum current are set to values suitable for the operation with a stable plasma. If, on the contrary, no stable plasma development is detected, the ignition test is repeated. To do so, it may be specific that the control device, following a failed ignition test, initially maintains a waiting phase before another ignition test is started. In doing so, it can be prevented that too high an energy input into the aqueous fluid and/or the biological tissue will occur.

Furthermore, the control device may be disposed to detect the electrical work that is to be understood as being integral to the electrical output over a period of time. For example, for detecting the electrical work, it is possible to use a specified time such as, for example, one second, within which the electrical power is upward-integrated or added up in small increments. For example, this may occur in intervals of seconds or also in deviating time intervals. In an advantageous embodiment, the control device reduces the waiting phase between two ignition tests or works without a waiting phase as long as the maximum permissible work for a given time interval has not yet been reached. In this manner, too great an energy input and also too long a wait time between successive ignition tests that are irritating or disruptive to the user are prevented.

Furthermore, the control device may be disposed to detect an approach of the electrode of the instrument toward the biological tissue that delimits the lumen. To do so, the electrical resistance between the electrode and the neutral electrode provided on the instrument or—alternatively separately—on the patient, can be measured, said resistance changing during the approach of the electrode toward the tissue. If such an approach is detected, the control device can start an ignition test. In an advantageous embodiment, it may be that the control device—if it is in a waiting phase between two ignition tests—reduces said waiting phase or works without waiting phase as long as the maximum permissible work for a given time interval has not yet been reached.

Furthermore, the apparatus according to the invention may be disposed to adapt not only the operating voltage and/or the power and/or the maximum current for the ignition phase but also the operating voltage and/or the power, and/or the maximum current for the subsequent operating phase, in view of the measured resistance and thus in an instrument-specific manner With individual, several or the sum of all of the aforementioned features it is possible to produce apparatus that automatically supply various connected instruments in such a manner that only minimal or no neuromuscular stimulations occur, and that, at the same time, good plasma ignition properties with minimal spark play, as well as a stable plasma maintenance, are achieved.

In particular for the control of the power output of an apparatus for supplying a medical instrument for the treatment of biological tissue due to the action of a plasma, the apparatus may comprise:

a generator for emitting a high-frequency voltage (RF voltage) and for delivering a high-frequency current (RF current), in which case the generator is connected to an outlet to which the instrument can be connected,
a power supply that is connected to the generator in order to supply said generator with an operating voltage, a control device for control of the generator and/or the power supply that comprises a measuring device for determining the high-frequency current delivered to the outlet, wherein the control device is disposed to specify—at least for a period of time—the maximum high-frequency current that can be delivered to the outlet or the power that can be delivered to the outlet and appropriately control the power supply and/or the generator.

The said period of time may incorporate the time in which a vapor bubble forms on a still wet electrode in contact with a fluid body, in which case an electrically conductive plasma forms in the vapor bubble. As long as a large area of the electrode is in contact with the fluid body, the control device limits the high-frequency current delivered to the outlet, i.e., the generator works within the current limitation, and the applied voltage is low. If a vapor bubble is formed, the electrical resistance surges upward by at least one order of magnitude, typically by several orders of magnitude, in which case a rapid decrease of the high-frequency current, a rapid increase of the high-frequency voltage and also an increase of the power delivered by the generator are involved.

Considering the apparatus mentioned hereinabove, the control device may be disposed to detect the decrease of the high-frequency current and/or the increase of the high-frequency voltage and newly set and in particular limit, based on this, the maximum value for the high-frequency current and/or the maximum power. The current measurement and/or the voltage measurement and the determination of the maximum power may occur periodically in short time intervals, for example, of 10 μs or 100 μs.

For the control of the operating voltage, for the limitation of the high-frequency current or the power, the power supply and/or the generator may comprise an appropriate control input that is connected to the control device. Via the control input, it is possible to specify the operating voltage to be output by the power supply and/or the current that can maximally be output by the power supply and/or the power that can maximally be output by the power supply. If the control input is provided on the generator, it is possible to specify the maximum high-frequency current that can be emitted by the generator and/or the power that can maximally be output by the generator and/or the high-frequency voltage that can maximally be output by the generator.

In order to detect a rapid current decrease that acts as indicator of the formation of a vapor bubble, the ratio of the high-frequency current detected at an actual time with respect to the high-frequency current of an earlier time can be used. The earlier time may be—in the event of a periodic current measurement—one or two earlier measurements. If the ratio is close to 1, there is no vapor bubble formation. If the ratio is substantially lower than 1, a vapor bubble formation exists. This may be considered as the signal for reducing or limiting the output of the generator. This measure stabilizes the plasma formation in that a premature detaching of the vapor bubble from the electrode is prevented. Also, the resultant spark is attenuated.

BRIEF DESCRIPTION OF THE DRAWINGS

Additional details of advantageous embodiments of the invention are the subject matter of the description, the claims or the drawings. They show in FIG. 1 a schematic representation of the apparatus according to the invention, a connected instrument and a biological object that is to be treated, FIG. 2 a schematic representation of the instrument in a hollow organ surrounded by aqueous fluid, FIG. 3 various instruments that can be attached to the apparatus according to FIG. 1, FIG. 4 diagrams for various settings of the instruments for igniting a plasma, FIG. 5 the behavior of current and voltage on an instrument when a plasma is ignited, FIG. 6 a diagram of various ignition scenarios, and FIG. 7 a diagram for illustrating various options of how the maximum current and the maximum power are functions of the measured resistance.

DETAILED DESCRIPTION

Figure 1:
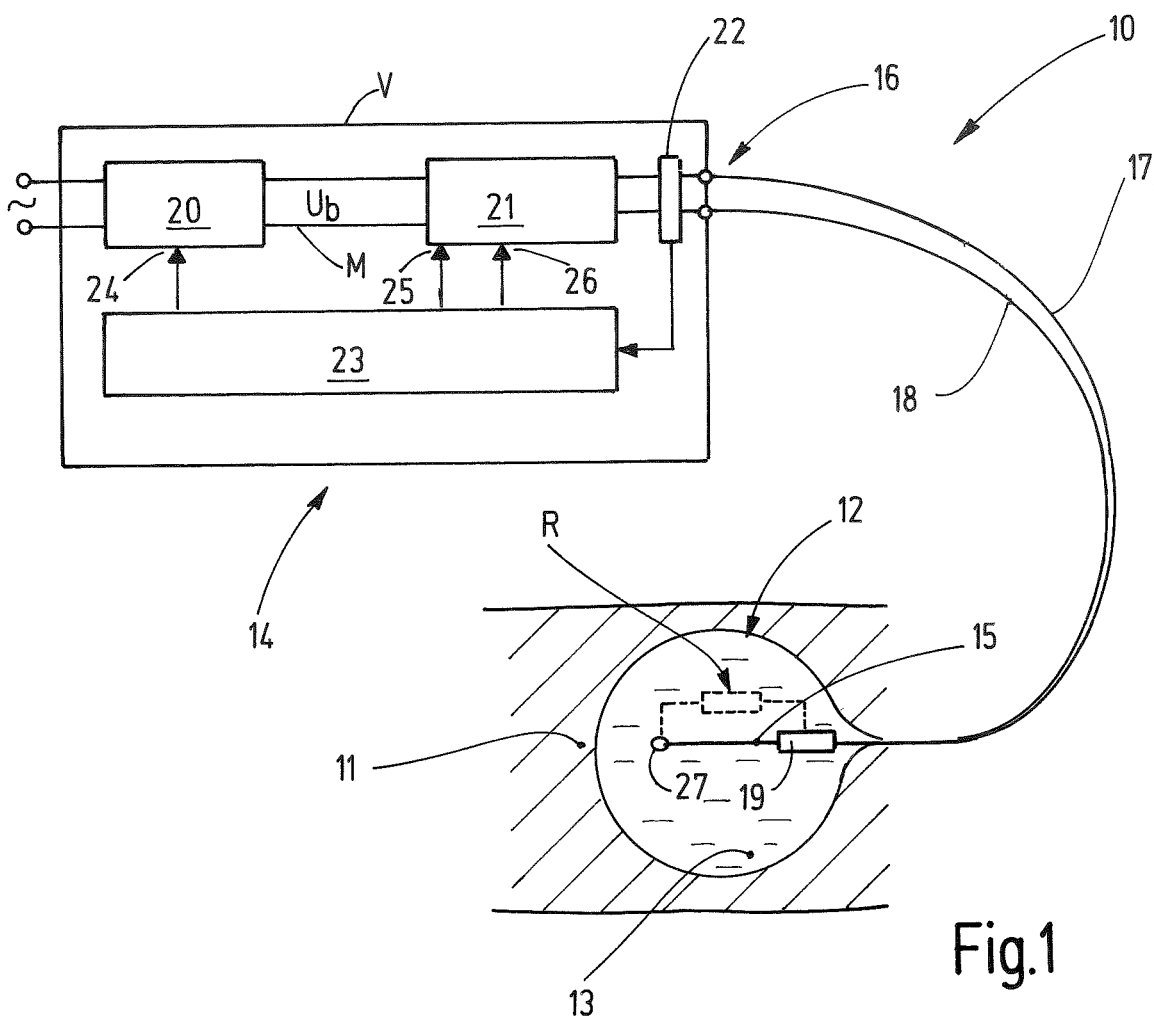

FIG. 1 shows an arrangement 10 for the treatment of biological tissue 11 that delimits a lumen 12. The lumen 12 may be the interior space of a hollow organ or also any cavity formed in the tissue 11. Typically, the lumen 12 is partially or completely filled with an aqueous fluid 13 such as, for example NaCl solution.

This arrangement 10 comprises an apparatus 14 that is disposed for supplying an instrument 15 with electrical current. To do so, the apparatus 14 has an outlet 16 to which the instrument 15 is connected or can be connected. If the instrument 15, as shown by FIG. 1, is a bipolar instrument, both poles of the outlet 16 are connected to the instrument 15. If, however, the instrument 15 is monopolar (see FIG. 3, bottom), a line 17 leads from one pole of the outlet 16 to the instrument 15, while the other line 18 leads from another pole of the outlet 16 to a counter-electrode 19 that is electrically connected to the biological tissue 11. The first line 17 is a high-frequency line, and the second line 18 is considered the neutral conductor.

The apparatus 14 comprises a power supply 20 that can be connected to an electrical power mains supply and provides an operating voltage $U_b$ between two lines V and M. This operating voltage is disposed to supply an assembly that forms a generator 21. From the operating voltage $U_b$ the generator 21 generates a high-frequency ac voltage that is output to the outlet 16. The frequency of the ac voltage may be set within the range from 100 kHz to 10 MHz.

For the detection of the current delivered to the instrument 15 and/or for the detection of the voltage applied to the outlet 16, there may be provided a measuring device 22, for example between the generator 21 and the outlet 16 or also as part of the generator 21. The measuring device 22 can determine—in addition to the voltage applied to the outlet 16 and/or the current flowing out through and in through the outlet 16—as, needed, also values derived therefrom such as, for example the ohmic resistance effective on the outlet 16 and/or the active power, apparent power and/or the reactive power. The detected and/or determined values (voltage, current, resistance, impedance, power, etc.) are transmitted to a control device 23. In doing so, the measuring device 22, can be configured—not only as depicted in FIG. 1—separate from the control device 23 but also be fully or partially a part of said control device. The control device 23 and the measuring device 22, like the generator 21 and the power supply 20, are to be understood to be function blocks that may be constructed on the same, as well as on separate, hardware assemblies.

The control device 23 is connected to a voltage regulation input 24 of the power supply 20. Via this voltage regulation input 24, the control device 23 specifies the nominal value for the operating voltage $U_b$ to the power supply 20. A regulating device provided in the power supply 20 regulates the actual value of the operating voltage $U_b$ to the nominal value, in which case temporary fluctuations may occur as part of the regulating process. This regulator may also be implemented in the control device 23.

Furthermore, the control device 23 is connected to a current limitation input 25 that may be provided on the generator 21 or on the power supply 20 or also on a current limitation assembly. The current limitation assembly may be arranged between the power supply 20 and the generator 21 or also between the generator 21 and the outlet 16. A signal that is output to the current limitation input 25 defines the current that can be maximally output to the outlet 16. When it is reached, the work of the power supply 20 and/or the generator 21 is adapted so as to not exceed the current limit.

Furthermore provided is a power limitation input 26 that may be provided on the generator 21, the power supply 20 or on an assembly interposed between the generator 21 and the power supply 20. The signal applied to the power limitation input 26 determines the maximum power that can be output at the outlet 16.

The voltage limitation input 24, the current limitation input 25 and the power limitation input 26 are to be understood to mean data channels that can be implemented in any desirable electrotechnical and data-transmitting manner It is also possible to dispense with a separate power limitation input and to achieve the power limitation by an adaptation of the signals on the voltage limitation input 14 and the current limitation input 25 to each other.

Figure 2:
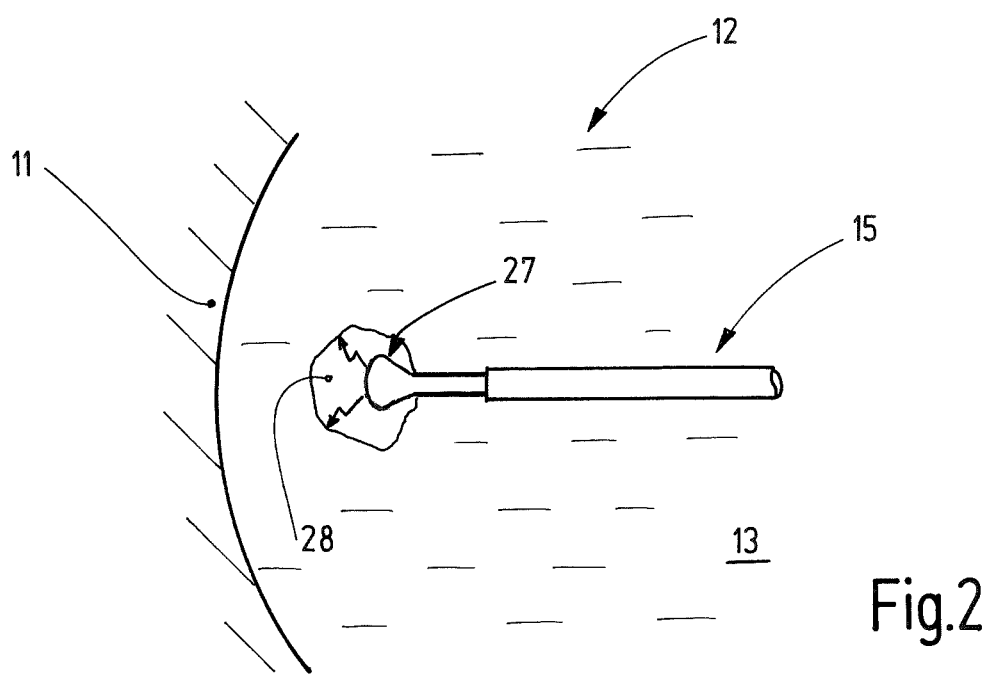

FIG. 2 is disposed to illustrate the instrument 15 and its use in the lumen 12. For example, the instrument may be an electrode 27 having the shape of a loop or a bracket, said electrode being connected to the line 17. When not ignited, the electrode 27 is wet and in full planar contact with the fluid 13, i.e., it is thus in electrical contact with said fluid. Therefore, a resistance R shown in dashed lines in FIG. 1 between the electrode 27 and the counter-electrode 19 can be measured, said resistance being essentially determined by the size and shape of the electrode 27. The resistance R is formed due to a combination of the resistance between the electrode 27 and the surrounding fluid 13, as well as the resistance of the current path through the fluid 13 up to the counter-electrode 19. If the electrode 27 is in the vicinity of the wall, there is an additional, parallel current path through the tissue. If the counter-electrode 19 is not a part of the instrument but needs to be separately applied to the patient, the electrical resistance is composed of only the series connection of the transition resistance between the electrode 27 and the surrounding fluid 13, as well as the resistance of the current path through the fluid 13 and the resistance through the body tissue up to the counter-electrode.

Figure 3:
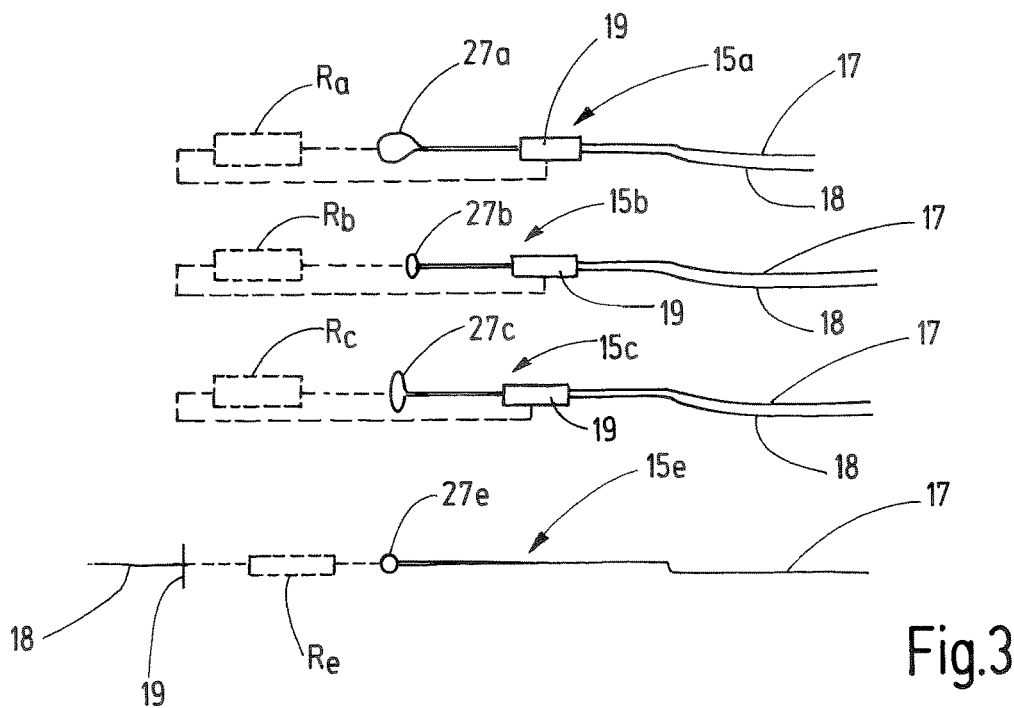

FIG. 3 symbolically illustrates various instruments 15a, 15b, 15c, 15e, respectively, and in dashed lines the resistance R relative to the corresponding neutral electrode. The instruments 15a to 15c are configured as monopolar instruments that are supplied only via one line 17; however, in the case of the bipolar instrument 15e, the counter electrode 19 referred to as the counter-electrode is provided directly on the instrument 15e that is then connected to both lines 17, 18. Furthermore, the instruments 15a to 15e differ from each other by the size and shape of their respective electrodes 27a, 27b, 27c, 27e. For example, the electrodes 27a, 27b, 27c, 27e may be configured as larger or smaller wire loops, ribbon loops, or as electrodes having a mushroom shape or another planar configuration.

If they are in contact with the fluid 13 or are connected to the apparatus 14, the instruments 15a to 15e have a characteristic resistance $R_a$, $R_b$, $R_c$, or $R_e$ to be measured between the electrode 27 and the counter-electrode 19, which resistance can be detected by the measuring device 22. For example, the detection may take place directly before a plasma is to be generated on the electrode 27 or also at the very beginning of such an ignition test, as long as the fluid 13 is still in uninterrupted contact with the electrode 27. It is also possible to perform a measuring cycle before an ignition test is performed.

For determining the resistance, a voltage is provided at the outlet 16. This voltage may correspond to that used for ignition of a plasma or it may also be lower than that. The current flowing at the outlet 16 can then be detected by the measuring device 22. Based on the measured voltage and the measured current, it is possible to determine the impedance and/or the resistance $R_{min}$. Before a first ignition test is performed, the latter has a value $R_a$, $R_b$, $R_c$, $R_e$, that can be viewed as being characteristic of the respective instrument 15a to 15e. In conjunction with this, reference is made to FIG. 7. This Figure shows on its horizontal axis various values $R_{min}$ namely $R_a$, $R_e$, $R_c$, $R_b$ for the different instruments 15a, 15e, 15c and 15b. Typically, these values are at 20 Ohm and 100 Ohm, in which case other values are not precluded.

Figure 7:
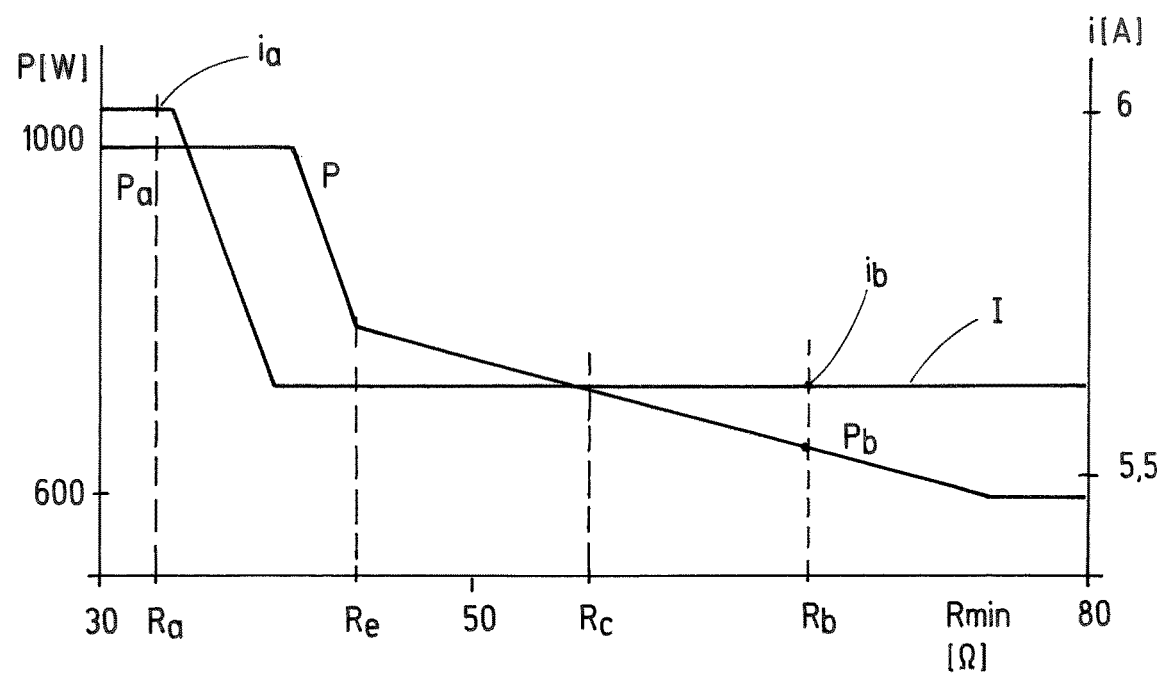

Furthermore, FIG. 7 is intended to illustrate the ignition control strategy that is implemented by the control device 23. Regarding this, reference is made to FIGS. 4 and 5, additionally and supplementally:

For the ignition of a plasma 28 within the fluid 13 (see FIG. 2) or on the wall of the lumen 12, the apparatus 14 provides high-frequency ac voltage that causes a current flow through the fluid 13 and, if the counter-electrode 19 is not attached to the instrument 15 itself but to the tissue 11, through the tissue. As a result of the direct wet contact of the fluid 13 to the electrode 27, the existing resistance is very small and a maximum of current flows. In doing so, the control device 23 limits the current in the power supply 20 or in the generator 21 to a value adapted to the respective instrument 15a, 15b, 15c or 15e. This value is a function of the resistance $R_a$ to $R_e$ that the measuring device 22 has determined just now or at a time preceding the ignition test.

With reference to graph I, FIG. 7 illustrates various maximum current values for the different instruments 15a, 15b, 15c or 15e displaying different resistances $R_a$ to $R_e$. Correspondingly, the generator output characteristic for the instrument 15b, for example, is set at the value $i_b$ in FIG. 4. According to FIG. 7, the maximum power $p_b$ for this instrument 15b is likewise set. As a result of this, the power according to the section $p_b$ is limited as soon as the current limitation is not active because a vapor bubble formation on the electrode 27 sets in and causes a current decrease. During the entire ignition process, the generator 21 is supplied with the operating voltage $U_{bb}$, said voltage preferably being set lower than the operating voltage $U_b$ that is provided for the generator while the plasma 278 is ignited. In the low-impedance state, the system is in current limitation state or in power limitation state; however, while the vapor bubble is forming, it is in voltage limitation state.

Figure 4:
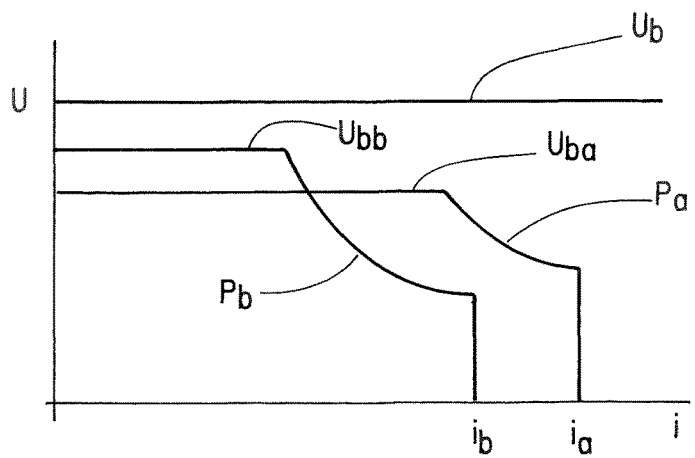

The reduction of the operating voltage $U_b$ to the value $U_{bb}$, the power limitation $p_b$ and the current limitation $i_b$ according to the diagram of FIG. 4 promote an instrument-appropriate ignition process with low spark formation and stable plasma development. Damaging effects that had to be accepted until now are prevented. This is also obvious from the simplified diagram according to FIG. 5 that deals, in particular, with the ignition of the plasma 28. In its left half, the diagram illustrates first—with the voltage U applied to the electrode 27—a high current $i_b$ that is specified by the current limitation ($i_b$ in FIG. 4, vertical branch of the characteristic). Because of the low resistance of a few 10 Ohms, only a low voltage is applied to the electrode 27b. The voltage specification in this state, however, is higher than the average. This is necessary because otherwise an initially occurring voltage excess would cause the voltage regulator to regulate the voltage downward to such a degree that the plasma might extinguish.

Figure 5:
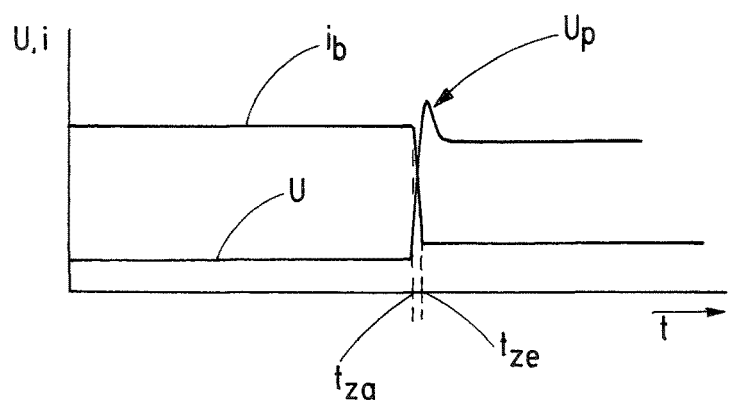

At a time $t_{za}$ a vapor bubble forms around the electrode 27, which vapor bubble is initially not electrically conductive and thus interrupts the current flow up to the voltage puncture, or at least greatly restricts the current flow. The abrupt current interruption or current reduction typically leads to a voltage peak on the generator 21 or the power supply 20, in particular due to the energy stored there in the form of inductances. In FIG. 5, this voltage peak is symbolized by $U_p$ and typically leads to an interfering light pulse generation and optionally a sound pulse generation that is also referred to as "spark play". Due to the reduction of the operating voltage to the value $U_{bb}$ (e.g., 550 V) and due to the restriction of the power to the instrument-specific value $p_b$ however, the spark play occurring when characteristic $p_b$ is passed as depicted by FIG. 4 is reduced to a minimum. Therefore, the voltage increases after time $t_{za}$ up to time $t_{ze}$ with minimal overshooting or without overshooting, whereas, in response, the current decreases to its operating value.

If, in contrast, another instrument, for example instrument 15a, is used and if this displays a different, lower resistance $R_a$ (see FIG. 7) in contact with the fluid 13, the control device 23 sets, for the ignition process according to FIG. 4, a higher maximum current $i_a$ and a higher maximum power $p_a$, as well as, again, an appropriate operating voltage $U_{ba}$ that may be higher or lower than $U_{bb}$ or may also correspond thereto. Again, an ignition process with minimal spark play and calm transition to the stable plasma maintenance is the result.

Furthermore, the control device 23 is disposed to interrupt an ignition test after an ignition test time $t_{vz}$ has elapsed, provided no ignition was detected. As can be inferred from the diagram of FIG. 6, thereafter a wait time $t_w$ is passed, during which no additional ignition test will be performed. Typically, the wait time $t_w$ is more than 100 ms, for example 0.8 s. In doing so, the power input into the fluid 13 and/or the tissue 11 is limited.

In order to increase convenience, there may be a provision that the control device 23 will maintain the wait time $t_w$ for a shorter period of time or not at all—under certain conditions. To do so, the control device 23 may be disposed to detect electrical work between the electrode 27 and the counter-electrode 19 for a certain detection period. For example, this detection period may be 1 s and the maximum work performed during said period may be 400 Ws. After such a detection interval has elapsed, the detection may be started anew. If now, for example, the first ignition test (on the extreme left in FIG. 6) is in a monitoring interval during which, in addition to the first ignition test during ignition time $t_{vz}$, there was performed another ignition test and the maximum electrical work has not yet been reached in the monitoring interval, the wait time $t_w$ can be abbreviated and the second ignition test otherwise to be performed after the wait time—as indicated by an arrow in FIG. 6—can be performed prematurely as the ignition test 30.

Figure 6:
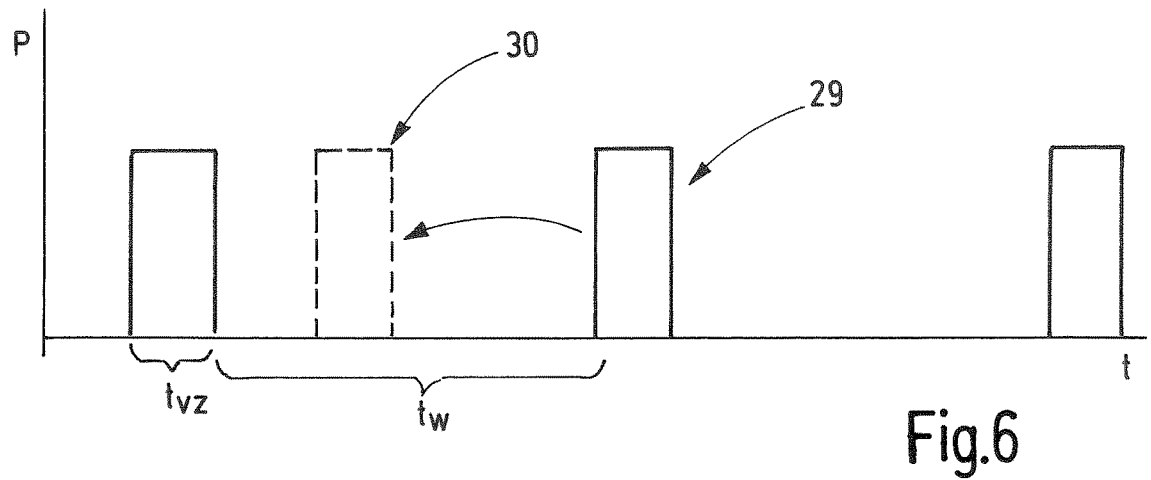

It is also possible to trigger the abbreviation or the premature interruption of the wait time interval $t_w$ whenever an approach of the electrode 27 to the biological tissue 11 is detected. Typically, this occurs with a change, e.g., increase of the electrical resistance, between the electrode 27 and the counter-electrode 19. Such a resistance change may be utilized as the triggering event for the interruption of the wait time interval, i.e., for performing an advanced ignition test 30 (FIG. 6). If needed, several ignition tests may be performed in rapid succession. In one modification of the embodiment this may be subject to the condition that—within a fixed monitoring time—a fixed limit for the performed electrical work has not yet been reached or has been exceeded.

An apparatus 14 for supplying a medical instrument 15 for the treatment of biological tissue 11 due to the action of a plasma 28 is disposed, in accordance with the invention, in a special manner for the ignition and the stable development of a plasma 28 on the electrode 27 of the instrument 15. To accomplish this, the apparatus 14 comprises a control device 23 that, during an ignition test, limits—preferably in an instrument-specific manner—the current deliverable to the instrument 15 and/or limits the electrical power to be output to the instrument 15, and/or, in doing so, works with a reduced operating voltage $U_{bb}$. With this measure, a rapid, stable plasma development with minimal spark play is achieved with a large variety of connectable instruments 15a-15e.

LIST OF REFERENCE SIGNS

10 Arrangement
11 Biological tissue
12 Lumen
13 Fluid
14 Apparatus
15 Instrument (with general reference)
15A-15e Instrument (with specific reference)
16 Outlet
17 First line
18 Second line
19 Counter-electrode
20 Power supply
V, M Lines
$U_b$ Operating voltage (e.g., 600 $V_p$)
21 Generator
22 Measuring device
23 Control device
24 Voltage regulation input
25 Current limitation input
26 Power limitation input
27 Electrode (with general reference)
27a-27e Electrode (with specific reference)
R Resistance
$R_{min}$ Minimal measured value of resistance R
$R_a$-$R_e$ Instrument-specific minimal resistance $R_{min}$
28 Plasma
I Instrument-specific maximum current characteristic
P Instrument-specific maximum power characteristic
$i_b$ Maximum current for instrument 15b
$p_b$ Maximum power for instrument 15b
$p_a$ Maximum power for instrument 15a
$U_{bb}$ Operating voltage for instrument 15b
$U_{ba}$ Operating voltage for instrument 15a
$t_{vz}$ Ignition test time (50 ms-500 s)
$t_w$ Wait time interval (0.5 s-1 s)
29 Later ignition test
30 Chronologically previous ignition test

The invention claimed is:

1. An apparatus for supplying a medical instrument for the treatment of biological tissue due to the action of a plasma, the apparatus comprising:
   a generator to output a high-frequency ac voltage to an outlet configured to be connected to the instrument,
   a power supply that is connected to the generator to supply said power supply with an operating voltage,
   a control device configured to control one or both of the generator and the power supply, with a measuring device configured to determine the electrical resistance of the instrument connected to the outlet when an electrode of the instrument is immersed in liquid but not ignited,
   wherein the control device is configured to specify, at least for a time period, at least one of the operating voltage, the power to be output to the instrument, and the maximum current deliverable to the instrument consistent with the determined electrical resistance, and to control one or both of the power supply and the generator accordingly in order to adapt an ignition process to different instruments with different electrode shapes based on the determined electrical resistance of the instrument.

2. The apparatus according to claim 1, wherein the power supply has a voltage regulation input that is connected to the control device.

3. The apparatus according to claim 1, wherein one or both of the power supply and the generator has a current limitation input that is connected to the control device.

4. The apparatus according to claim 1, wherein one or both of the power supply and the generator has a power limitation input that is connected to the control device.

5. The apparatus according to claim 1, wherein the control device comprises an operating status detection arrangement that is configured to detect a start of an ignition test during which the ac voltage delivered by the generator to the instrument develops a plasma on the instrument.

6. The apparatus according to claim 5, wherein the control device is configured to specify, during the ignition test, a nominal value for the operating voltage, said value being greater than during operation after the ignition test.

7. The apparatus according to claim 1, wherein the control device comprises an operating status detection arrangement that is disposed to detect an end of an ignition test or an extinguishing of a plasma, during which the ac voltage delivered to the instrument by the generator has resulted in the development of the plasma on the instrument.

8. The apparatus according to claim 1, wherein the control device comprises an operating status detection arrangement that is configured to detect an end of an ignition test, during which the ac voltage delivered to the instrument by the generator does not result in the development of a plasma on the instrument.

9. The apparatus according to claim 1, wherein the control device is configured, after a failed ignition test, to maintain a specified pause interval during a wait phase and to then start another ignition test.

10. The apparatus according to claim 9, wherein the control device is configured to detect an electrical work supplied to the instrument.

11. The apparatus according to claim 10, wherein the control device is configured to detect an approach of the instrument placed in a lumen toward the biological tissue and to interrupt the wait phase and start another ignition test, provided the control device is in the wait phase.

12. The apparatus according to claim 1, wherein the control device is configured to specify one or any combination of the operating voltage, the power deliverable to the instrument, and the maximum current deliverable to the instrument during an operating phase following an ignition phase, consistent with the resistance measured before ignition of the plasma, and to control one or both of the power supply and the generator accordingly.

13. An apparatus for supplying a medical instrument for the treatment of biological tissue due to the action of a plasma, the apparatus comprising:
   a generator to output a high-frequency ac voltage to an outlet configured to be connected to the instrument,
   a power supply that is connected to the generator to supply said power supply with an operating voltage,
   a control device configured to control one or both of the generator and the power supply, with a measuring device configured to determine the electrical resistance of the instrument connected to the outlet,
   wherein the control device is configured to specify, at least for a time period, at least one of the operating voltage, the power to be output to the instrument, and the maximum current deliverable to the instrument consistent with the determined electrical resistance, and to control one or both of the power supply and the generator accordingly,
   wherein the control device is configured, after a failed ignition test, to maintain a specified pause interval during a wait phase and to then start another ignition test,
   wherein the control device is configured to detect an electrical work supplied to the instrument,
   wherein the control device is configured to detect an approach of the instrument placed in a lumen toward the biological tissue and to interrupt the wait phase and start another ignition test, provided the control device is in the wait phase.

14. An apparatus for supplying a medical instrument for the treatment of biological tissue due to the action of a plasma, the apparatus comprising:
   a generator to output a high-frequency ac voltage to an outlet configured to be connected to the instrument,
   a power supply that is connected to the generator to supply said power supply with an operating voltage,
   a control device configured to control one or both of the generator and the power supply, with a measuring device configured to determine the electrical resistance of the instrument connected to the outlet,
   wherein the instrument comprises an electrode and the electrical resistance of the instrument comprises a characteristic resistance, wherein the control device is configured to detect the type of instrument or a shape of the electrode by determining the characteristic resistance of the instrument,
   wherein the control device is configured to specify, at least for a time period, at least one of the operating voltage, the power to be output to the instrument, and the maximum current deliverable to the instrument consistent with the determined characteristic resistance of the instrument, and to control one or both of the power supply and the generator accordingly.

* * * * *